(12) United States Patent
Eshelman

(10) Patent No.: US 8,005,772 B2
(45) Date of Patent: Aug. 23, 2011

(54) SEGMENT-PRESERVING CROSSOVER IN GENETIC ALGORITHMS

(75) Inventor: Larry Eshelman, Ossining, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 912 days.

(21) Appl. No.: 11/914,991

(22) PCT Filed: Jun. 15, 2006

(86) PCT No.: PCT/IB2006/051933
§ 371 (c)(1),
(2), (4) Date: Nov. 20, 2007

(87) PCT Pub. No.: WO2006/136987
PCT Pub. Date: Dec. 28, 2006

(65) Prior Publication Data
US 2008/0195565 A1 Aug. 14, 2008

Related U.S. Application Data

(60) Provisional application No. 60/692,646, filed on Jun. 21, 2005.

(51) Int. Cl.
G06F 15/18 (2006.01)
G06N 3/00 (2006.01)
G06N 3/12 (2006.01)
(52) U.S. Cl. .................................................. 706/13
(58) Field of Classification Search ............... 706/13
See application file for complete search history.

(56) References Cited

U.S. PATENT DOCUMENTS

| | | | |
|---|---|---|---|
| 4,935,877 A | 6/1990 | Koza | |
| 5,435,309 A * | 7/1995 | Thomas et al. ............... 600/310 |
| 6,477,519 B1 | 11/2002 | Shackleford | |
| 2004/0081977 A1 | 4/2004 | Hsu et al. | |
| 2004/0167721 A1 | 8/2004 | Murakawa et al. | |
| 2005/0086007 A1 * | 4/2005 | Shackleford et al. ........... 702/19 |

OTHER PUBLICATIONS

J. Rowland and J. Taylor, "Adaptive Denoising in Spectral Analysis by Genetic Programming", Evolutionary Computation, 2002. CEC'02. Proceedings of the 2002 Congress on, IEEE 2002, pp. 133-38.*

R. Jarvis and R. Goodacre, "Genetic algoritm optimization for pre-processing and variable selection of specroscopic data", Bioinformatics, vol. 21 No. 7 2005, pp. 860-68, Advance Access publication Oct. 28, 2004.*

Kuzmanovski et al., "Optimization of Supervised Self-Organizing Maps With Genetic Algorithms for Classification of Urinary Calculi", Journal of Molecular Structure, Elsevier, Amsterdam, NL, vol. 744-747, Jun. 3, 2005, pp. 833-838.

(Continued)

*Primary Examiner* — Wilbert L. Starks, Jr.
*Assistant Examiner* — Vincent M Gonzales

(57) ABSTRACT

Cross over (S560) in a genetic algorithm (128) is adapted for deriving an optimal mask (S540), or set of segments of a line. Each mask of a chromosome is subject to cross over with the respective mask of the other parent. Any overlapping part, whether a filtering (320) or pass-through part (350), is retained in the child (334) to preserve commonality. The part is preferably, potentially extended, according to one parent or the other, as decided pseudo-randomly (430). In a preferred application, spectrums of candidate blood constituents are masked for fitting to ensemble spectrums of test blood samples (S610, S620). The developed masks are applicable to constituent spectrums to create masked spectrums (S710) which are then applicable to an actual blood sample to be analyzed (S720).

21 Claims, 7 Drawing Sheets

OTHER PUBLICATIONS

Melab et al., "Parallel GA-Based Wrapper Feature Selection for Spectroscopic Data Mining", Parallel and Distributed Processing Symposium, Proceedings International, IPDPS 2002, Abstracts and CD-ROM FT. Lauderdale, FL USA Apr. 15-19, 2002, Los Alamitos, CA, USA, IEEE Comput. Soc., US, Apr. 15, 2002, pp. 201-208.

Ye et al., "Raman Spectrum Baseline Identification and Its Optimization Using Genetic Algorithm", Intelligent Control, 2004, Proceedings of the 2004 IEEE International Symposium on Taipei, Taiwan Sep. 2-4, 2004, Piscataway, NJ, USA, IEEE Sep. 2, 2004, pp. 489-494.

Madden et al., "Machine Learning Methods for Quantitative Analysis of Raman Spectroscopy Data", Opto-Ireland 2002: Optics and Photonics Technologies and Applications Sep. 5-6, 2002 Galway, Ireland, vol. 4876, No. 1, 2002, pp. 1130-1139.

Lavine et al., "Innovative Genetic Algorithms for Chemoinformatics", Chemometrics and Intelligent Laboratory Systems, Elsevier Science Publishers, B.V., Amsterdam, NL, vol. 60, No. 1-2, Jan. 28, 2002, pp. 161-171.

Koo et al., "Measurement of Glucose in Human Blood Serum Using Raman Spectroscopy", IEEE, Apr. 1998, 2 pages.

Rovithakis et al., "A Genetically Optimized Artificial Neural Network Structure for Feature Extraction and Classification of Vascular Tissue Fluorescence Spectrums", Dept. of Electronic & Computer Engineering Technical University of Crete, 73100 Chania, Crete, Greece, IEEE, 2000, pp. 107-111.

* cited by examiner

SEGMENT-PRESERVING CROSSOVER IN GENETIC ALGORITHMS

CROSS REFERENCE TO RELATED APPLICATIONS

This application claims the benefit of International Application Number PCT/IB2006/051933, filed Jun. 15, 2006, and U.S. Provisional Application Ser. No. 60/692,646 filed Jun. 21, 2005 which are incorporated herein in whole by reference.

The present invention relates to crossover in genetic algorithms, and, more particularly to crossover that preserves the commonality between masks of the parents.

Genetic algorithms are search and optimization techniques based on the principle of survival of the fittest. Representations of proposed solutions to a problem to which the genetic algorithm is applied are known as chromosomes. As in nature, the chromosomes may mutate, or pairs of them may combine in a crossover or "recombination" operation to form one or more children chromosomes. The problem to be solved by the genetic algorithm is such that the fitness of each chromosome, toward solving the problem, can be measured or assessed. In an iterative process, the least fit chromosomes are eliminated and the fittest chromosomes survive and are used to produce, via mutation and crossover, offspring that are variants of their parents. This process is repeated until a halting criterion is reached. Then, typically the best chromosome found so far is chosen as the "solution" to the problem.

The genetic algorithm is a powerful search technique that uses the population diversity to control the breadth of the search. The tradeoff between diversity (trying many variations) and focus (exploiting what seems to be working) is achieved primarily by the crossover operator that preserves what is common between the two parents (i.e., is respectful) while trying variations of what isn't common.

There have been a number of crossover operators designed for particular problems, e.g., crossover operators that preserve bits in a bit representation, ranges in a real-valued representation, tours in a traveling salesman representation, sets in a subset representation. The emphasis herein is in preserving commonality among two broken lines, or two masks, aligned in parallel for comparison. The goal is to find an optimal set of line segments or, posed another way, an optimal mask.

Thus, for instance, if the mask spans a range or continuum subject to a particular process, filtering parts of the mask might indicate where, along the continuum, the process is to be performed, or not be performed. If we are looking for an optimal mask or set of masks, and have a way to evaluate fitness of any arbitrary mask or set of masks, the present inventive crossover procedure can be employed.

One example for which this inventive crossover procedure can be implemented is to optimize input to a matching procedure. A sample of a substance, such as a blood sample, whose composition is unknown, can be subjected to radiation such as infrared or laser. Raman spectroscopy uses a monochromatic light source, such as a laser. Plotting intensity versus frequency shift results in a locus of points that constitutes the Raman spectrum of the sample. Blood constituents and their concentrations can be determined from the spectrum. The determination can be made by separately obtaining spectrums for pure samples of candidate components, and comparing or matching them to the overall spectrum of the sample, i.e., the ensemble spectrum. The intensities of the ensemble spectrum where the component spectrums are matched indicate concentration. Multivariate analysis using several blood components concurrently in the matching procedure is typically favored over univariate analysis.

Matching spectrums in this fashion has been used to noninvasively analyze blood of diabetics, who need frequent analyses of their blood, particularly glucose concentration.

The matching can be performed electronically using linear or nonlinear multivariate analysis such as partial least squares (PLS) or hybrid linear analysis (HLA), but is hampered by noise mainly from the unknown constituents of the particular blood sample and by other noise such as communication noise. As a consequence of the noise, only certain segments of the pure glucose Raman spectrum contribute to the ensemble spectrum. Masking out the non-contributory segments would enhance the matching procedure utilized, but it would be difficult to derive optimal component masks analytically.

The present inventive crossover operator is designed to solve a problem of this type. A chromosome can be provided with several masks for respective candidate components of the blood sample. The fitness of the chromosome is assessable by testing its masks against an ensemble spectrum of a test blood sample of known composition. Moreover, since the actual constituents of a patient's blood differ from patient to patient, a versatile set of masks is desired. It is therefore preferable to use multiple test blood samples in deriving a set of masks.

According to one aspect of the invention, spectrums of candidate components of a substance of unknown composition are masked for subsequent matching of the masked spectrums to an ensemble spectrum of said substance. For crossover in a genetic algorithm, masks of one of the candidate components of respective parent chromosomes are compared. Both masks include at least one filtering range. In forming a mask of a child chromosome, a part of the mask that overlaps with respect to the at least one filtering range is retained. The retained overlapping part, according to a rule of said algorithm, is selectively extended to create a filtering range in forming the child chromosome mask as a proposed mask. The comparing, retaining and extending are repeated for any remaining candidate components of the parent chromosomes.

In another aspect of the invention, a sample of a substance of unknown composition is spectroscopically analyzed. In preparation, a collective fitting of a plurality of masked spectrums of respective candidate components of the substance to ensemble spectrums of associated test samples of the substance is iteratively performed. The test samples have known composition. As a result of the fitting, a set of optimal masked component spectrums for subsequent collective fitting to an ensemble spectrum of the sample of the substance of unknown composition is derived. An output of the iterative performing is outputted.

Details of the invention disclosed herein shall be described with the aid of the figures listed below, wherein.

Figure 1:
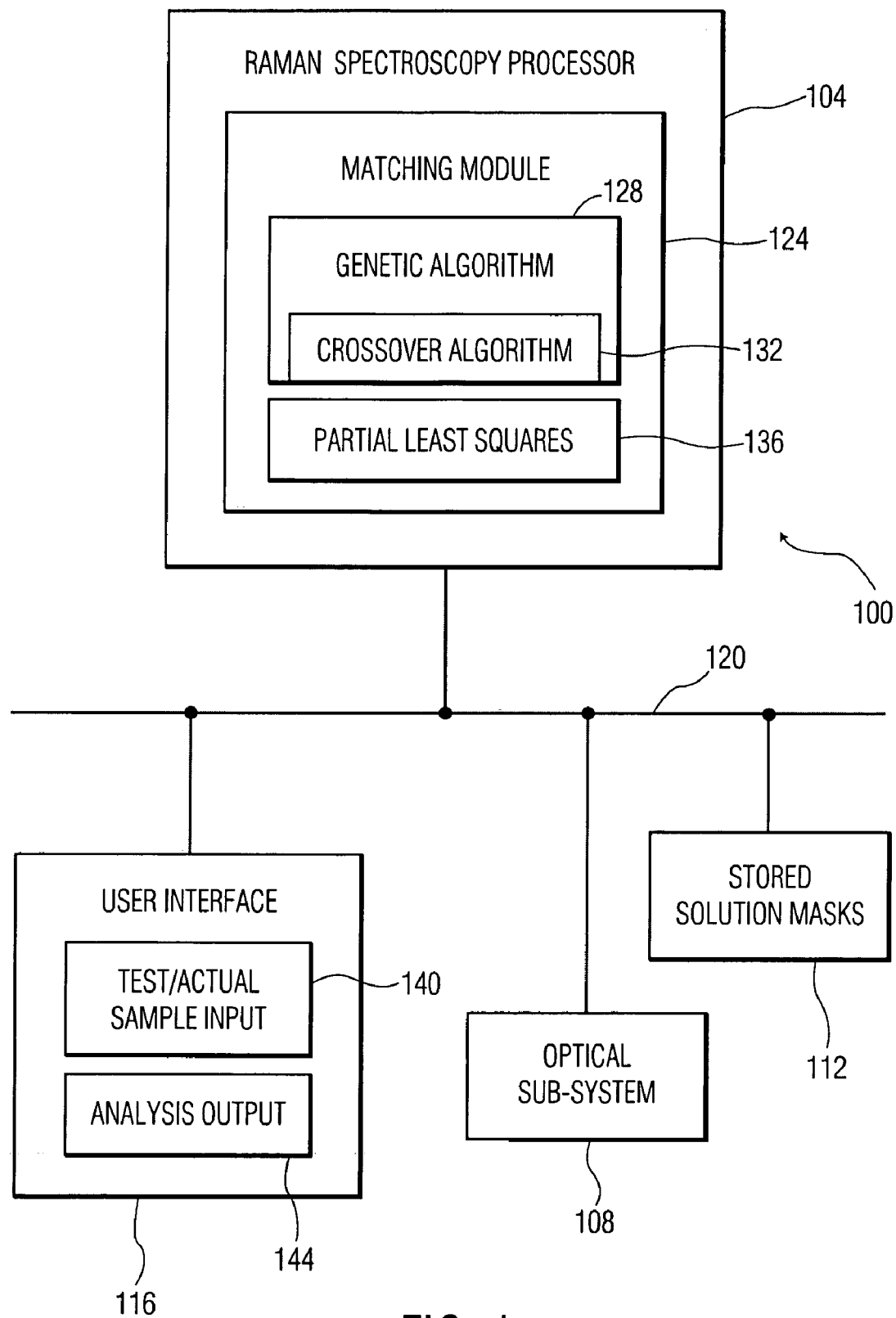
FIG. 1 is a schematic diagram of a Raman spectroscopy system according to the present invention.

FIG. 1 shows an example of a Raman spectroscopy system 100 according to the present invention, which includes a Raman spectroscopy processor 104, an optical sub-system 108, stored solution masks 112 and a user interface 116, all connected on a data and control bus 120 which serves as an interface to the various elements on the bus. The processor 104 includes a matching module 124 for matching sets of masked component spectrums to ensemble spectrums. The matching module features a genetic algorithm 128 embodying a mask-based crossover algorithm 132, and a multivariate analysis algorithm 136 such as partial least squares. Masks of a chromosome selected as the solution to the genetic algorithm 128 are stored as the stored solution masks 112, which may be implemented with any kind of read-only or random access memory, volatile or non-volatile. The user interface 116 includes user-actuatable controls 140 for indicating that a test or actual blood sample has been placed within the system 100 for analysis. The user interface 116 further includes a screen or other output mechanism 144 for presenting the results of the analysis. Although the present invention is discussed herein within the context of Raman spectroscopy, a spectrum used in connection with the present invention may be produced by other means, such as by infrared spectroscopy. It is noted, in addition, that although the present, inventive crossover operator with segment preservation is couched in the context of a spectrum-matching for blood analysis, the intended scope of the invention is not limited to such application.

Figure 2:
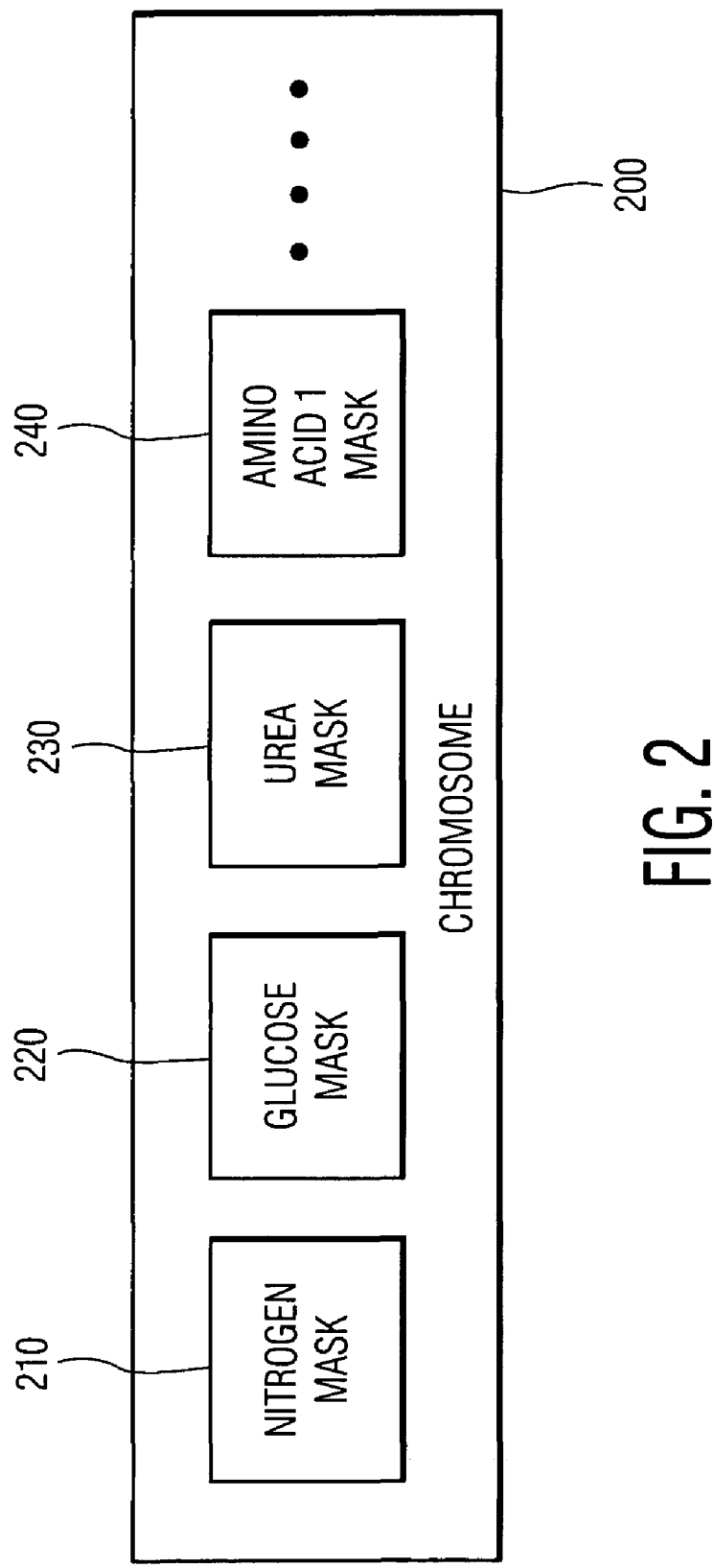
FIG. 2 is a conceptual diagram of a chromosome according to the present invention.

FIG. 2 illustrates a typical chromosome 200 usable in accordance with the present invention. The chromosome 200 contains a nitrogen mask 210, a glucose mask 220, a urea mask 230, and a mask 240 for an amino acid. The chromosome 200 may, and typically would, include various other masks for other candidate components such as peptides, alcohol or other constituents.

Figure 3:
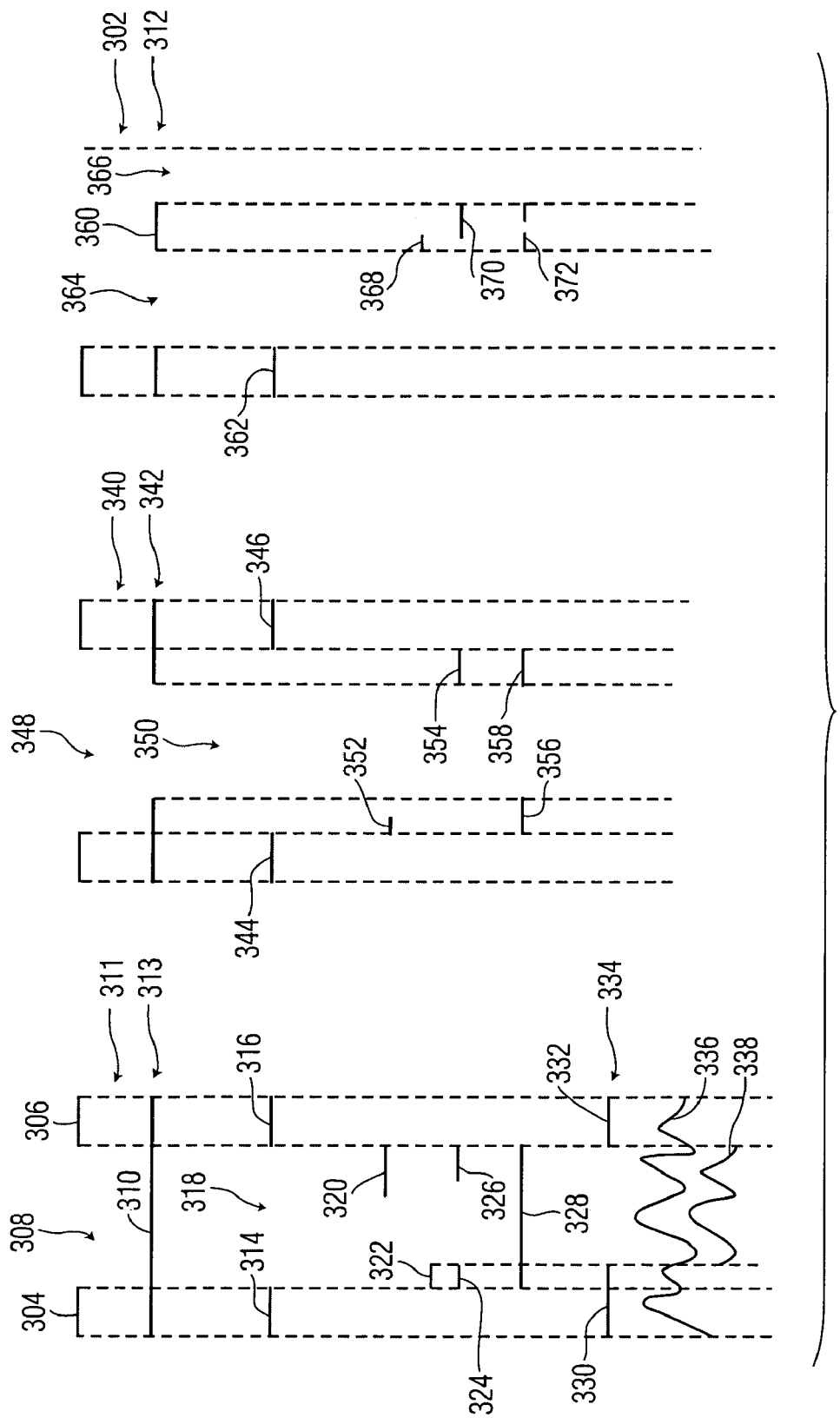
FIG. 3 is a conceptual diagram of exemplary masks according to the present invention.

FIG. 3 provides three examples of how the crossover algorithm 132 forms a mask for a child chromosome in accordance with the present invention. In example 1, the mask 302 of the first parent chromosome in the crossover procedure has two filtering ranges 304, 306, and an intervening non-filtering range 308. The mask 310 of the second parent chromosome 312 consists of a single filtering range and no non-filtering range. A filtering range may be seen as corresponding to regions where a process is not to be performed, the non-filtering range identifying a region where the process is to be performed. Alternatively, the designations can, at the outset, be reversed. The broken vertical lines are merely intended to offer visual alignment for the viewer of FIG. 3.

To identify commonality of the parents 302, 312 which we seek to preserve, the two masks 311, 313 are compared for overlap. A region 314 is one overlapping part, and a region 316 is another overlapping part.

To further diversify so as to lead to a solution of the genetic algorithm 128, a gap 318 between the overlapping parts 314, 316 is potentially filled partially or wholly, preferably according to a pseudo-random procedure that takes account of one or both parents 302, 312. The probability of selecting one parent or the other can be equal or weighted. Out of respect for the vital overlapping information, the filling preferably seeks to extend an overlapping segment 314, 316. As three possible examples of how one or both of the overlapping parts 314, 316 can be extended, FIG. 3 shows extensions 320, 322 as two possibilities and extension 324, 326 as a third possibility. In each of these three possibilities, the pseudo-random procedure happened to choose the second parent 312 to fill the gap 318. Moreover, each of the three possibilities fills the gap 318 merely partially. To what extent a gap is filled can also be subject to pseudo-random outcome. In a fourth possibility, an extension 328 is also derived based on the choosing of the second parent 312, but a subsequent pseudo-random selection has filled the gap 318 completely. Assuming the second possibility is realized, the overlapping part 314 is extended by the extension 322 to form the filtering regions 330, 332 of a mask 334 of a child chromosome.

When the child chromosome having the mask 334 is tested to assess fitness of its containing chromosome, the mask 334 is applied to a Raman spectrum 336 of a pure component to produce a masked component spectrum 338.

The second example demonstrates a case in which masks 340, 342 of the parents 302, 312 have a mutual gap, indicated in FIG. 3 by the gap between the vertical broken lines. A mutual gap may be seen as an overlapping part of non-filtering ranges. All mutual gaps are preferably left unfilled, based again on commonality. Accordingly any extension of an overlapping part 344, 346 into an overlap of non-filtering ranges 348, 350, i.e., the mutual gap, is precluded. Three possibilities of extensions to the retained overlapping parts 344, 346 are shown as extension 352, extension 354 and extensions 356, 358, respectively. Another possibility is no extension, depending upon the outcome of the pseudo-random selection between parents 302, 312.

Example 3 shows a filtering range 360 without overlap that is not adjacent to any overlapping part 362. Moreover, since the filtering range 360 is separated from any overlapping part by a mutual gap, the filtering range cannot serve to extend any overlapping part 362. Yet, by pseudo-random discovery, we want to give the respective parent 312 the opportunity to pass on to any child chromosome part or all of the filtering range 360. In one implementation, a non-overlapping part of a mask that borders on a mutual gap 364, 366 may be retained if the respective parent 302, 312 is selected pseudo-randomly. Three instances 368, 370, 372 of such retention are shown.

Figure 4:
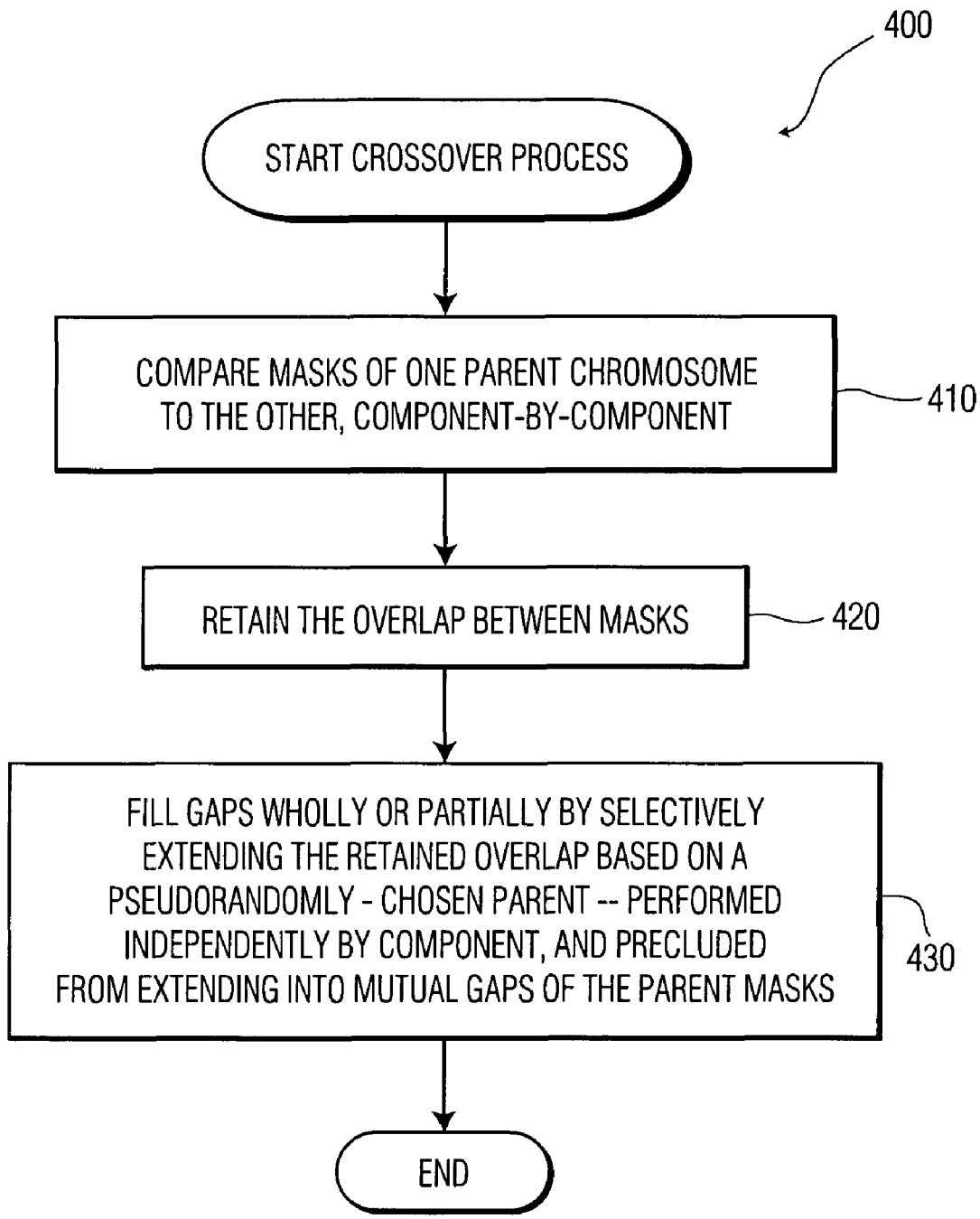
FIG. 4 is a flow chart of a crossover process according to the present invention.

FIG. 4 sets forth, by way of illustrative and non-limitative example, the above-discussed steps 410, 420, 430 of a crossover operator 400 according to the present invention. The three steps 410, 420, 430 are each performed with respect to a pair of parent chromosomes for one candidate component, and are repeated for the next candidate component of the pair, until no candidate component remains. Step 430 can also be implemented with the above-mentioned rule for selectively retaining part or all of a non-overlapping filtering region 360 bordering on a mutual gap 364, 366.

Figure 5:
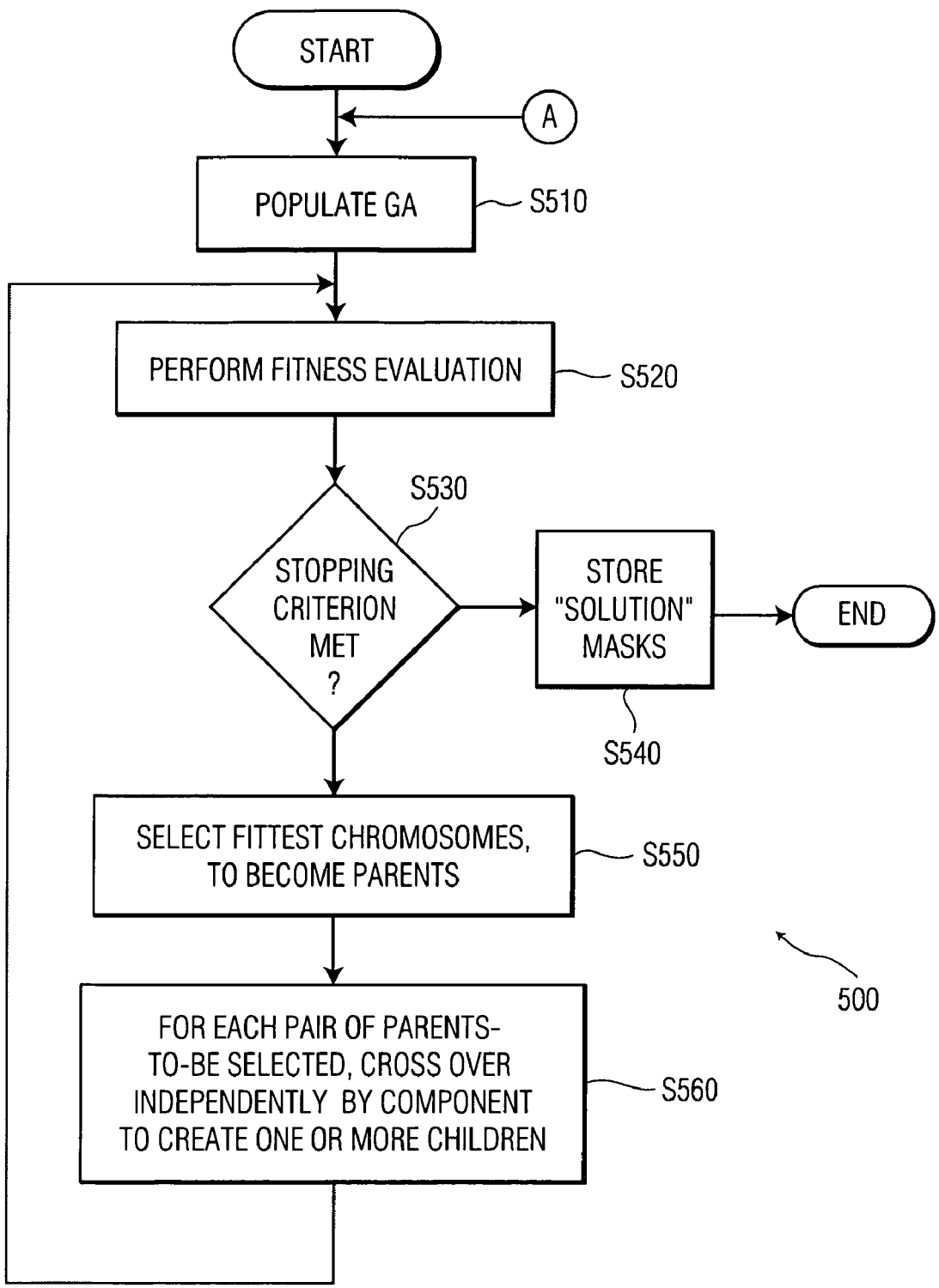
FIG. 5 is a flow chart of a mask derivation process according to the present invention.

The inventive crossover process 400 operates within the genetic algorithm 128 to prepare a set of optimal masks by means of an exemplary mask preparation process 500, as set forth in FIG. 5.

The instant crossover process 400 operates point-wise in alignment, i.e., with crossover operating strictly perpendicularly, the two masks of respective parents being disposed in parallel and in alignment. Thus, if the initial population consists of two parents that are identical component-wise as to masks, all filtering and non-filtering ranges overlap, and crossover consequently has no diversity by which to flourish. That initial diversity can be introduced by mutating with elitism, i.e., so that the chromosome that is to be mutated is retained. Alternatively, particular masks may be known to have some effectiveness based, for example, on trial and error.

The first step, therefore, is to populate the genetic algorithm (step S510). This may be done by creating masks at random for the initial chromosomes that are to constitute the initial population.

A fitness evaluation routine is applied, chromosome-by-chromosome, to the initial population to provide each chromosome with a fitness value (step S520). In most applications of genetic algorithms, once a fitness value is generated for a chromosome, the value is unchanging. Thus, once fitness values are generated for the initial population, subsequent invocations of the fitness evaluation routine need only create fitness values for new chromosomes. However, if a sufficient amount of noise accompanies the fitness evaluation process, it may be preferable, with each generation, to evaluate each member of the population. Likewise, if test samples are changing during genetic algorithm 128 processing, all population members are evaluated in each generation.

If a predetermined stopping criterion is met (step S530), the currently fittest chromosome may be considered a "solution," and the masks of the chromosome, i.e., the solution masks, are stored (step S540). The stopping criterion typically might be a fitness threshold or iteration threshold. The iteration threshold may simply be a set number of iterations, or may be a set number of iterations without improvement, i.e., without the fittest chromosomes changing from iteration to iteration. The masks selected as a "solution" are optionally subject to testing on further test samples to gauge the effectiveness of the solution masks.

If the stopping criterion is not met (step S530), a selection is made among the population for chromosomes to serve as parents (step S550). The crossover procedure with segment preservation is executed to create one or more child chromosomes (step S560). Mutations of some chromosome(s) might likewise be created typically at random and infrequently. Processing then returns to the fitness evaluation routine (step S520).

Figure 6:
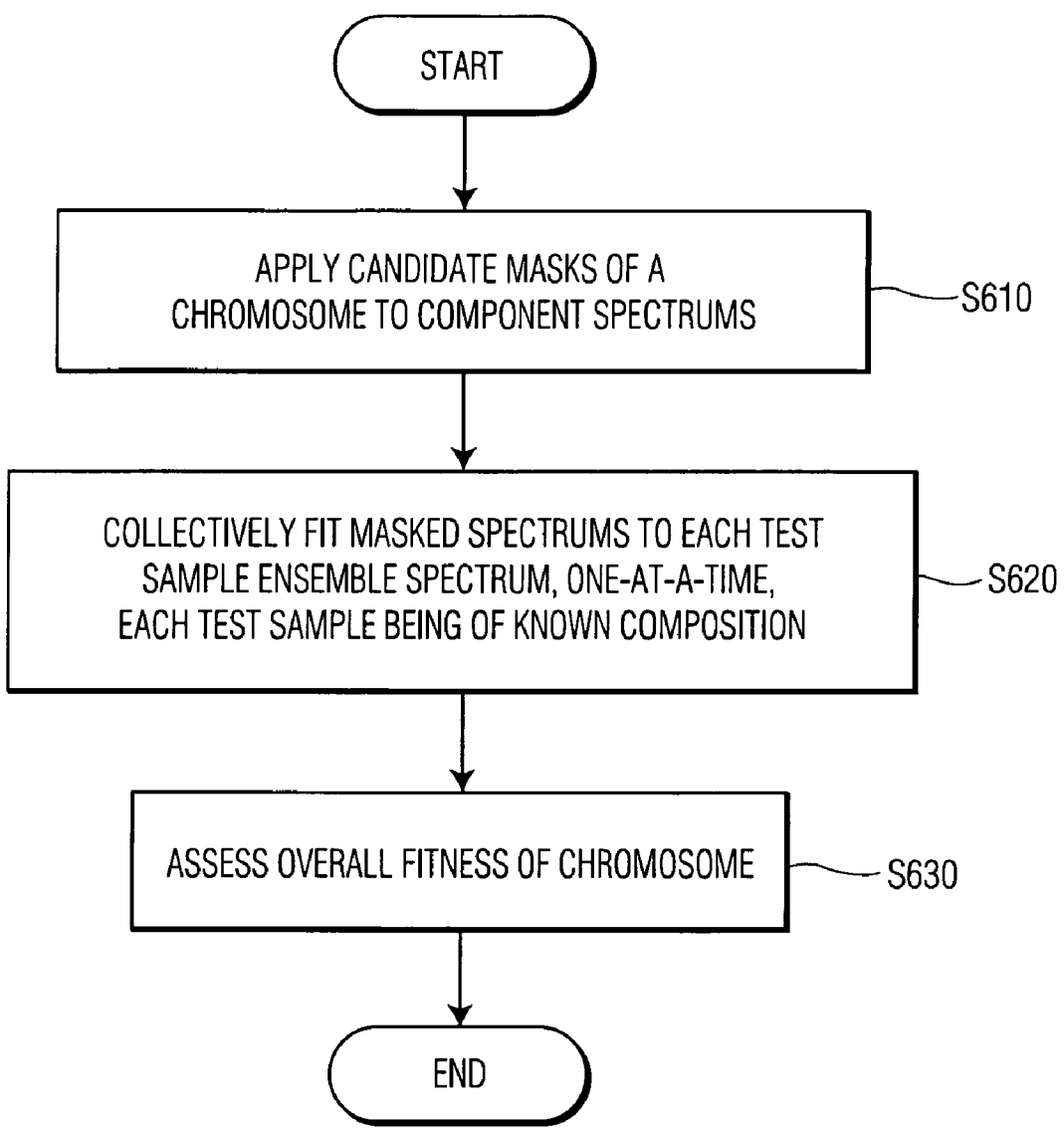
FIG. 6 is a flow chart of a chromosome fitness evaluation procedure according to the present invention.

FIG. 6 is an example of a fitness evaluation routine 600 that can be implemented as step S520. The current blood test samples are each of known composition. Each yields a Raman ensemble spectrum, for example by means of the optical sub-system 108. Thus, spectrums of pure candidate components can be collectively fitted to or matched against the ensemble spectrum to analyze composition of the test sample. Advantageously, according to the present invention, the candidate component Raman spectrums are first masked by respective, candidate component masks in the chromosome being evaluated.

As a first step in the fitness evaluation routine 600, the masks of a chromosome to be evaluated are applied to component Raman spectrums 336 for corresponding components. This creates a set of masked spectrums (step S610).

The subsequent collective fitting of the chromosome's masked spectrums to the test ensemble Raman spectrum is performed for a first test sample, as by the partial least squares algorithm 136, and likewise for a second test sample, until matching has been made against each test sample (step S620).

For any given test sample, a matching that identifies more components, or more of the important components, e.g., glucose, may be earn a higher fitness value for its chromosome. Alternatively or in addition, component concentrations implied by the positioning of component spectrums upon matching can be compared to the actual known concentrations for the test sample to assess fitness of the chromosome (step S630).

Figure 7:
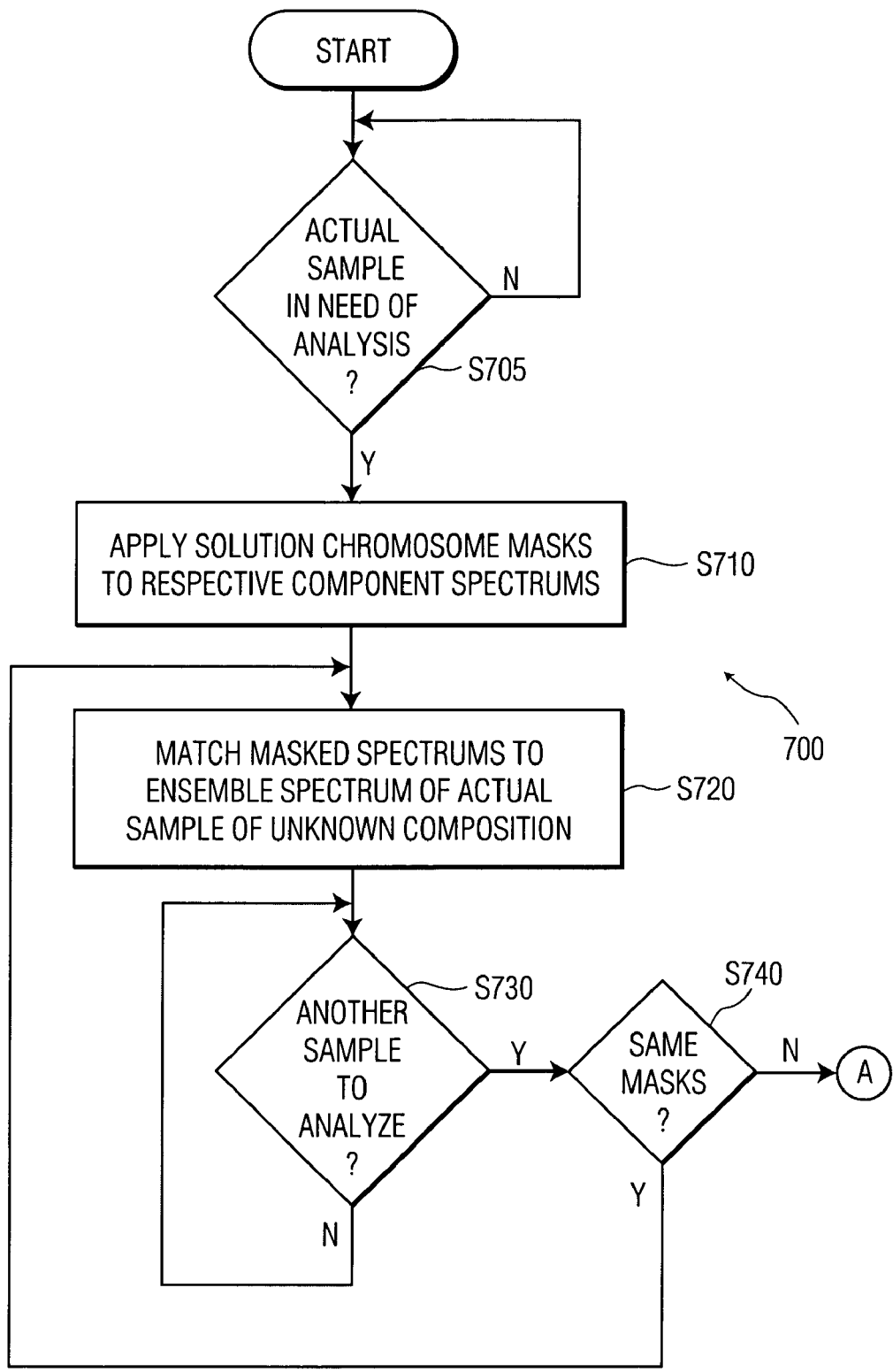
FIG. 7 is a flow chart of Raman spectroscopy analysis according to the present invention.

FIG. 7 demonstrates an example of a procedure 700 for Raman spectroscopy analysis of an unknown blood sample according to the present invention. When an actual sample of unknown composition is to be analyzed (step S705), the solution masks are applied to respective pure component Raman spectrums (step S710). The masked spectrums are then collectively matched to the Raman ensemble spectrum of the actual sample of unknown composition (step S720), preferably using the identical matching algorithm that was utilized in step S720. The solution masks are influenced by the test samples chosen, and multiple sets of solution masks can be developed by the mask preparation process 500 to accommodate different kinds of patients, e.g., diabetics, infants, people potentially under the influence of alcohol, people of different cultures whose blood may differ due to diet. If the same set of masks is to be applied against another actual sample, processing returns to step S720 (steps S730, S740). On the other hand, whenever a new, different set of masks is desired, processing returns to the mask preparation process 500 (steps S730, S740) to prepare the new set of masks (step S540). A return is then made back to the analysis procedure 700 to apply the new set of masks.

An alternative embodiment utilizes, instead of one pure spectrum per component, multiple spectrums each at a different concentration of the component. For example, an aqueous solution of glucose at a particular concentration is irradiated to produce a Raman spectrum. This is done for different concentrations, and for various other possible blood components at different concentrations. From among all the candidate spectrums, the best match is found to the ensemble spectrum, using PLS 136 for example. For any given candidate component, the matching outputs a respective concentration, which may be 0% if the blood yielding the ensemble spectrum lacks that component.

In this alternative embodiment, the chromosome 200 is provided with a set of respective masks for various concentrations of the blood sample, and this is done for each candidate component of the chromosome. Step 410 of the crossover process compares not only component by component, but concentration by concentration. Crossover is segregated in step S560 not only by component but by concentration. Mask preparation in accordance with FIG. 5 assesses the fitness of the chromosome 200 by matching its masked spectrums against an ensemble spectrum. This is done for each member of a group of ensemble spectrums, each ensemble spectrum pertaining to a test blood sample of known composition. For each matching operation, the blood composition results are compared to the known blood sample composition. Fitness of a chromosome's collection of masks can thus be assessed overall based on the test blood samples. The test blood samples preferably vary with respect to component concentrations, so as to provide a wide variety of permutations by which to assess a chromosome's overall fitness.

While there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for masking spectrums of candidate components a substance of unknown composition for subsequent matching of the masked spectrums to an ensemble spectrum of said substance, said method comprising the acts of:

a) a processor comparing, for crossover in a genetic algorithm, masks of one of said candidate components of respective parent chromosomes, both of said masks including at least one filtering range;

b) the processor retaining, in forming a mask of a child chromosome, a part of said masks that overlaps with respect to said at least one filtering range;

c) the processor selectively extending the retained overlapping part, according to a rule of said algorithm, to create a filtering range in said forming of the child chromosome mask as a proposed mask for said masking; and d) the processor repeating the acts a) through c) for any remaining one of said candidate components of said parent chromosomes.

2. The method of claim 1, wherein the selective extending includes:

pseudo-randomly choosing one of said parent chromosomes and retaining, in forming said child chromosome mask, a part of the respective mask of the chosen chromosome that does not overlap, as to filtering range, the respective mask of the other of said parent chromosomes.

3. The method of claim 2, wherein the retained non-overlapping part borders on the overlapping part in the chosen chromosome, so that said non-overlapping part borders on the retained overlapping part in said selective extending of the retained overlapping part.

4. The method of claim 2, wherein whether the retained non-overlapping part is external to each of said at least one filtering range of the chosen chromosome generally depends upon an outcome of said choosing.

5. The method of claim 1, wherein each of said masks has at least one non-filtering range that borders on one or more of the respective said at least one filtering range, said extending being precluded from extending into any overlap between the respective non-filtering ranges of said corresponding two.

6. The method of claim 1, further comprising:

further retaining, in forming said mask of a child chromosome, a range external to each of said at least one filtering range of said masks, if such an external range exists; and, if said external range exists, additionally retaining, in forming said child chromosome mask, a non-overlapping part of one of said masks that borders on said external range.

7. The method of claim 6, further comprising pseudo-randomly choosing said one of said masks for the additional retaining of the part of the respective mask.

8. An apparatus for masking spectrums of candidate components of a substance of unknown composition for subsequent matching of the masked spectrums to an ensemble spectrum of said substance, said apparatus being configured for performing acts comprising:

a) comparing, for crossover in a genetic algorithm, masks of one of said candidate components of respective parent chromosomes, both of said masks including at least one filtering range;

b) retaining, in forming a mask of a child chromosome, a part of said masks that overlaps with respect to said at least one filtering range;

c) selectively extending the retained overlapping part, according to a rule of said algorithm, to create a filtering range in said forming of the child chromosome mask as a proposed mask for said masking; and d) repeating acts a) through c) for any remaining one of said candidate components of said parent chromosomes.

9. The apparatus of claim 8, wherein the selective extending includes:

pseudo-randomly choosing one of said parent chromosomes; and retaining, in forming said child chromosome mask, a part of the respective mask of the chosen chromosome that does not overlap, as to filtering range, the respective mask of the other of said parent chromosomes.

10. The apparatus of claim 9, wherein the retained non-overlapping part borders on the overlapping part in the chosen chromosome, so that said non-overlapping part borders on the retained overlapping part in said selective extending of the retained overlapping part.

11. The apparatus of claim 9, wherein whether the retained non-overlapping part is external to each of said at least one filtering range of the chosen chromosome generally depends upon an outcome of said choosing.

12. The apparatus of claim 8, wherein each of said masks has at least one non-filtering range that borders on one or more of the respective said at least one filtering range, said extending being precluded from extending into any overlap between the respective non-filtering ranges of said corresponding two.

13. The apparatus of claim 8, configured for:

further retaining, in forming said mask of a child chromosome, a range external to each of said at least one filtering range of said masks, if such an external range exists; and, if said external range exists, additionally retaining, in forming said child chromosome mask, a non-overlapping part of one of said masks that borders on said external range.

14. The apparatus of claim 13, further configured for pseudo-randomly choosing said one of said masks for the additional retaining of the part of the respective mask.

15. A tangible computer-readable medium having stored thereon a computer program product for masking spectrums of candidate components of a substance of unknown composition for subsequent matching of the masked spectrums to an ensemble spectrum of said substance, said product being executable by a processor and comprising instructions for performing acts comprising:

a) comparing, for crossover in a genetic algorithm, masks of one of said candidate components of respective parent chromosomes, both of said masks including at least one filtering range;

b) retaining, in forming a mask of a child chromosome, a part of said masks that overlaps with respect to said at least one filtering range;

c) selectively extending the retained overlapping part, according to a rule of said algorithm, to create a filtering range in said forming of the child chromosome mask as a proposed mask for said masking; and d) repeating acts a) through c) for any remaining one of said candidate components of said parent chromosomes.

16. The tangible computer-readable medium of claim 15, wherein the selective extending includes:

pseudo-randomly choosing one of said parent chromosomes; and retaining, in forming said child chromosome mask, a part of the respective mask of the chosen chromosome that does not overlap, as to filtering range, the respective mask of the other of said parent chromosomes.

17. The product of claim 15, wherein each of said masks has at least one non-filtering range that borders on one or more of the respective said at least one filtering range, said extending being precluded from extending into any overlap between the respective non-filtering ranges of said corresponding two.

18. A method for spectroscopically analyzing a sample of a substance of unknown composition, said sample having an ensemble spectrum, the method comprising:

a processor iteratively performing a collective fitting of a plurality of masked spectra of respective candidate components of the substance to ensemble spectrums of associated test samples of the substance, said test samples having known composition, to derive a set of optimal masked component spectra for subsequent collective fitting to said ensemble spectrum; and outputting an output of the iterative performing, wherein the processor iteratively performs the collective fitting by crossing over masks of parent candidate components to produce a child candidate component that retains a part of the masks of the parent candidate components that overlaps and selectively extends the retained part to further include a non-overlapping part of the mask of one of the parent candidate components.

19. An apparatus for spectroscopically analyzing a sample of a substance of unknown composition, said sample having an ensemble spectrum said apparatus comprising:

a matching module configured to iteratively perform a collective fitting of a plurality of masked spectra of respective candidate components of the substance to ensemble spectrums of associated test samples of the substance, said test samples having known composition, to derive a set of optimal masked component spectra for subsequent collective fitting to said ensemble spectrum; and an interface for outputting an output of the iterative performing, wherein the matching module iteratively performs the collective fitting by crossing over masks of parent candidate components to produce a child candidate component that retains a part of the masks of the parent candidate components that overlaps and selectively extends the retained part to further include a non-overlapping part of the mask of one of the parent candidate components.

20. The apparatus of claim 19, wherein said matching module is further configured such that a masked spectrum of a component changes pseudo-randomly from one iteration to a next iteration for at least some of the iterations of the iterative.

21. A tangible computer-readable medium having stored thereon a computer program product for an apparatus for spectroscopically analyzing a sample of a substance of unknown composition, said sample having an ensemble spectrum, said product being executable by a processor to carry out acts comprising:

iteratively performing a collective fitting of a plurality of masked spectra of respective candidate components of the substance to ensemble spectrums of associated test samples of the substance, said test samples having known composition, to derive a set of optimal masked component spectra for subsequent collective fitting to said ensemble spectrum; and outputting an output of the iterative performing, wherein iteratively performing the collective fitting includes crossing over masks of parent candidate components to produce a child candidate component that retains a part of the masks of the parent candidate components that overlaps and selectively extends the retained part to further include a non-overlapping part of the mask of one of the parent candidate components.

* * * * *